US011690998B2

(12) United States Patent
O'Neill

(10) Patent No.: US 11,690,998 B2
(45) Date of Patent: Jul. 4, 2023

(54) METHODS OF TREATING BACTERIAL INFECTIONS

(71) Applicant: TheraDep Technologies, Inc., Palo Alto, CA (US)

(72) Inventor: Liam O'Neill, Midleton (IE)

(73) Assignee: THERADEP TECHNOLOGIES, INC., Palo Alto, CA (US)

( * ) Notice: Subject to any disclaimer, the term of this patent is extended or adjusted under 35 U.S.C. 154(b) by 766 days.

(21) Appl. No.: 16/176,546

(22) Filed: Oct. 31, 2018

(65) Prior Publication Data

US 2019/0126027 A1 May 2, 2019

Related U.S. Application Data

(60) Provisional application No. 62/579,367, filed on Oct. 31, 2017.

(51) Int. Cl.
| | | |
|---|---|---|
| *A61N 1/04* | (2006.01) | |
| *A61K 9/12* | (2006.01) | |
| *A61P 31/04* | (2006.01) | |
| *A61K 9/16* | (2006.01) | |
| *A61K 47/14* | (2017.01) | |
| *A61K 9/00* | (2006.01) | |

(Continued)

(52) U.S. Cl.
CPC .......... *A61N 1/0412* (2013.01); *A61K 9/0014* (2013.01); *A61K 9/12* (2013.01); *A61K 9/16* (2013.01); *A61K 41/00* (2013.01); *A61K 47/14* (2013.01); *A61L 2/0011* (2013.01); *A61L 2/14* (2013.01); *A61P 31/04* (2018.01); *A61K 31/43* (2013.01); *A61K 31/545* (2013.01); *A61K 31/65* (2013.01); *A61K 31/7036* (2013.01); *A61L 2202/11* (2013.01)

(58) Field of Classification Search
CPC ...... A61N 1/0412; A61K 9/0014; A61K 9/12; A61M 2037/0007
See application file for complete search history.

(56) References Cited

U.S. PATENT DOCUMENTS

| | | |
|---|---|---|
| 4,929,319 A | 5/1990 | Dinter et al. |
| 6,565,558 B1 | 5/2003 | Lindenmeier et al. |

(Continued)

FOREIGN PATENT DOCUMENTS

| | | |
|---|---|---|
| EP | 1 498 128 A1 | 1/2005 |
| EP | 1705965 A1 | 9/2006 |

(Continued)

OTHER PUBLICATIONS

Bogaerts et al., "Gas Discharge Plasmas and Their Applications," *Spectrochimica Acta Part B*, vol. 57, pp. 609-658 (2002).

(Continued)

*Primary Examiner* — Dung T Ulsh
(74) *Attorney, Agent, or Firm* — Bookoff McAndrews, PLLC

(57) ABSTRACT

Methods for treating a bacterial infections, including drug-resistant bacterial infections, of a patient are described. The methods may include applying a non-thermal plasma and a liquid simultaneously to infected tissue of the patient, the liquid comprising at least one antibiotic and/or antiseptic and a penetration enhancing agent; wherein the non-thermal plasma has a frequency between 200 kHz and 600 kHz.

20 Claims, 1 Drawing Sheet

(51) Int. Cl.
  *A61L 2/00*     (2006.01)
  *A61K 41/00*    (2020.01)
  *A61L 2/14*     (2006.01)
  *A61K 31/43*    (2006.01)
  *A61K 31/65*    (2006.01)
  *A61K 31/7036*  (2006.01)
  *A61K 31/545*   (2006.01)

(56) References Cited

U.S. PATENT DOCUMENTS

| | | | |
|---|---|---|---|
| 6,632,193 B1 * | 10/2003 | Davison | A61B 18/1485 604/22 |
| 7,201,935 B1 | 4/2007 | Claude et al. | |
| 7,455,892 B2 | 11/2008 | Goodwin et al. | |
| 7,758,537 B1 * | 7/2010 | Brunell | A61N 1/06 604/22 |
| 9,060,513 B2 * | 6/2015 | Hoffmann | A61P 31/00 |
| 2002/0020024 A1 | 2/2002 | Schmitz et al. | |
| 2003/0087985 A1 | 5/2003 | Hubbell et al. | |
| 2004/0176749 A1 | 9/2004 | Lohmann et al. | |
| 2006/0084158 A1 | 4/2006 | Viol | |
| 2007/0029500 A1 | 2/2007 | Coulombe et al. | |
| 2008/0118734 A1 | 5/2008 | Goodwin et al. | |
| 2008/0199513 A1 | 8/2008 | Beretta et al. | |
| 2008/0237484 A1 | 10/2008 | Morfill et al. | |
| 2011/0112528 A1 * | 5/2011 | Stieber | H05H 1/2439 606/41 |
| 2011/0159273 A1 | 6/2011 | Lukowski et al. | |
| 2012/0009231 A1 | 1/2012 | Herbert et al. | |
| 2012/0089084 A1 * | 4/2012 | O'Keeffe | A61L 26/0066 523/105 |
| 2012/0171354 A1 | 7/2012 | O'Neill et al. | |
| 2015/0314036 A1 | 11/2015 | O'Keeffe et al. | |
| 2016/0166818 A1 * | 6/2016 | Kalghatgi | A61K 9/0021 604/24 |
| 2016/0236002 A1 * | 8/2016 | Dirk | A61N 1/0468 |
| 2017/0246440 A1 * | 8/2017 | Kalghatgi | A61L 2/14 |
| 2017/0354616 A1 * | 12/2017 | Roe | A61K 33/00 |
| 2018/0154039 A1 | 6/2018 | O'Keeffe et al. | |

FOREIGN PATENT DOCUMENTS

| | | |
|---|---|---|
| EP | 2666544 A1 | 11/2013 |
| JP | 2006-501356 | 1/2006 |
| JP | 2008-501069 | 1/2008 |
| WO | WO 89/01790 | 3/1989 |
| WO | WO 98/22153 | 5/1998 |
| WO | WO 2002/028548 A2 | 4/2002 |
| WO | WO 2003/097245 A2 | 11/2003 |
| WO | WO 2005/106477 A2 | 11/2005 |
| WO | WO 2005/110626 A1 | 11/2005 |
| WO | WO 2006/048650 A1 | 5/2006 |
| WO | WO 2006/116252 A2 | 11/2006 |
| WO | WO 2007/106212 A1 | 9/2007 |
| WO | WO 2009/101143 A1 | 8/2009 |
| WO | WO 2009/146432 A1 | 12/2009 |
| WO | WO 2010/022871 A1 | 3/2010 |
| WO | WO 2010/105829 A1 | 9/2010 |
| WO | WO 2010/146438 A1 | 12/2010 |
| WO | WO 2012/080835 A2 | 6/2012 |
| WO | WO 2017/136334 A1 | 8/2017 |

OTHER PUBLICATIONS

Chekmareva et al., Bulletin of Experimental Biology and Medicine, 129: 392-395 (2000).
Department of Defense, Blast Injury Research Program Coordinating Office, "Minimizing the Impact of Wound Infections Following Blast-Related Injuries," 2016.
Fridman et al., "Comparison of Direct and Indirect Effects of Non-Thermal Atmospheric-Pressure Plasma on Bacteria," *Plasma Processes and Polymers*, vol. 26: pp. 370-375 (2007).
Fridman et al., "Plasma Chem Plasma Process," 26: 425-442 (2006).
Guerin et al., "Plasma Polymerization of Thin Films: Correlations Between Plasma Chemistry and Thin Film Character", *Langmuir*, vol. 18 pp. 4118-4123 (2002).
Heinlin et al. "Plasma Medicine: Possible Applications in Dermatology," *Journal of the German Society of Dermatology*, 8, pp. 1-9 (2010).
International Search Report in priority application PCT/IB10/01439, dated Nov. 16, 2010 (2 pages).
International Search Report in PCT/US2017/015805 dated Jun. 26, 2017 (6 pages).
Ladwig et al., "Atmospheric Plasma Deposition of Glass Coatings on Aluminum," *Surface & Coatings Technology*, vol. 201, pp. 6460-6464 (2007).
Laroussi, Mounir, "Plasma Medicine: A Brief Introduction," Plasma, 1, pp. 47-60 (2018).
Lloyd et al. "Gas Plasma: Medical Uses and Developments in Wound Care," Plasma Processes and Polymers, 7, pp. 194-211 (2010).
Massarweh et al., "Electrosurgery: History, Principles, and Current and Future Uses", *J. Am. Coll. Surg.*, vol. 202, pp. 520-530 (2006).
Mennel et al., "Helium (Argon) Plasma Coagulation in Neurosurgery. Morphology of Tissue Damage and Reparation," *Exp Toxic Pathol*, vol. 54, pp. 255-263 (2002).
Okazaki et al., "Appearance of Stable Glow Discharge in Air, Argon, Oxygen and Nitrogen at Atmospheric Pressure Using a 50 Hz Source", *J. Phys. D; Appl. Phys.* vol. 26, pp. 889-892 (1993).
Reich et al., "Argon Plasma Coagulation (APC) for Endo-Urological Procedures: Ex-Vivo Evaluations of Hemostatic Properties", *European Urology*, vol. 44, pp. 272-276 (2003).
Roth et al., "Atmospheric Pressure Plasma Sources," Ch. 15, pp. 37-73 in Industrial Plasma Engineering, vol. 2: Applications to Non-thermal Plasma Processing, Institute of Physics Publishing (2001).
Shoulders et al., "Collagen Structure and Stability", *Annu. Rev. Biochem*, vol. 78, pp. 929-959 (2009).
Supplementary European Search Report for European Application No. 10789079, dated Aug. 22, 2014 (1 page).
U.S. Appl. No. 16/074,365, filed Jul. 31, 2018 (40 pages).

* cited by examiner

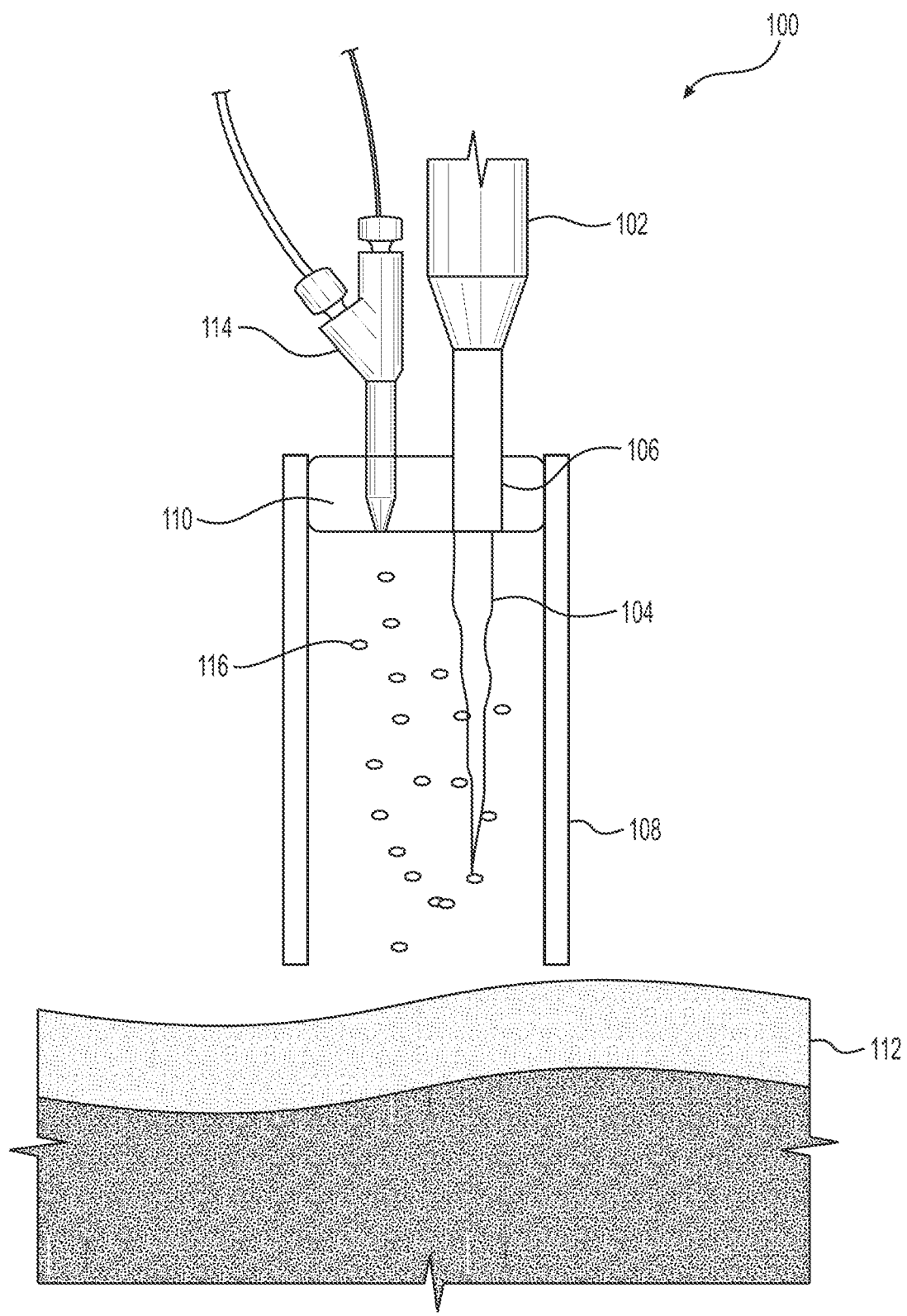

METHODS OF TREATING BACTERIAL INFECTIONS

CROSS-REFERENCE TO RELATED APPLICATIONS

This application claims the benefit of priority under 35 U.S.C. § 119 of U.S. Provisional Application No. 62/579,367, filed on Oct. 31, 2017, which is incorporated by reference herein in its entirety.

TECHNICAL FIELD

The present disclosure generally relates to methods of treating bacterial infections, e.g., drug resistant bacterial infections, with a non-thermal plasma.

BACKGROUND

In general, bacterial wound infections are a constant challenge in injury care cases. According to the U.S. Department of Defense's 2016 International State of the Science Meeting for Blast Injury Research, approximately 25% of wounds become infected. Within that group, there is an increasing emergence of drug resistant bacteria and multi-drug resistant organisms (MDROs) detected in soldiers that served in Iraq and Afghanistan. A recent study of 2,079 combat patients admitted to two (level V) hospitals showed that 14% tested positive for drug-resistant Gram-negative bacteria. Similar results are seen in civilian hospitals where drug-resistant and multi-drug resistant bacteria are now commonly encountered. For example, methicillin-resistant *Staphylococcus aureus* (MRSA) is now prevalent in many hospitals worldwide and a recognized term among the general public.

Bacteria have developed numerous defenses against antibiotics. Many of these defense mechanisms are based on blocking the bacteria's exposure to antibiotics. For example, surface receptors on the outside of the bacteria may become altered, or the bacteria may be encased within a protective biofilm. Biofilm is the term used to describe an agglomeration of bacteria which secrete an extracellular matrix composed of extracellular DNA, proteins, and polysaccharides. The biofilm can act as a polymeric shield that prevents antibiotics from migrating through and contacting the bacteria. This protective barrier may protect the bacteria present deep within the biofilm. Once a biofilm has formed, the bacteria can be difficult to treat with standard antibiotics. Further, the presence of a biofilm has been linked to impaired wound healing and fatalities.

Despite a decline in the efficacy of some antibiotics and a need for development of new antibiotics, few come to market. Current products in development are limited and prone to the same drug-resistant concerns. Alternative approaches such as phage therapy or antimicrobial peptides tend to be limited by a high degree of selectivity or degradation by the patient's immune system. Current treatments for MDRO infections use cocktails of antibiotics, yet this approach is also susceptible to reduced efficacy over time.

SUMMARY

The present disclosure includes methods of treating bacterial infections of a patient, including, e.g., drug-resistant bacterial infections. For example, the method may comprise applying a non-thermal plasma and a liquid simultaneously to infected tissue of the patient, the liquid comprising at least one antibiotic and a penetration enhancing agent, wherein the non-thermal plasma has a frequency between 200 kHz and 600 kHz. In some examples herein, the infected tissue includes drug-resistant bacteria. The penetration enhancing agent may be chosen from dimethyl sulfoxide, azone, urea, an essential oil, a pyrrolidone, a fatty acid, an oxazolidinone, a terpene, a perpenoid, or a mixture thereof.

In some examples herein, the penetration enhancing agent and/or the antibiotic may be in liquid form. According to some embodiments of the present disclosure, the liquid comprises a carrier together with the penetration enhancing agent and the antibiotic(s). For example, the carrier may be chosen from water, an alcohol, a lipid, an organic solvent, or a mixture thereof, e.g., wherein the antibiotic(s), the penetration enhancing agent, or both are dissolved in the carrier. In at least one example, the penetration enhancing agent is in liquid form, and the at least one antibiotic is dissolved in the penetration enhancing agent.

According to some aspects of the present disclosure, the at least one antibiotic comprises tobramycin, vancomycin, gentamicin, ampicillin, amoxiocillin, sulfamethoxazole/trimethoprim, carbapenem, penicillin, chloramphenicol, cephalosporin C, cephalexin, cefaclor, cefamandole and ciprofloxacin, dactinomycin, actinomycin D, daunorubicin, doxorubicin, idarubicin, penicillin, piperacillin, streptomycin, a cephalosporin, quinolone, anthracycline, mitoxantrone, a tetracycline, ticarcillin, bleomycin, plicamycin, mitomycin, polymyxin, ciprofloxacin, macrolide, fluoroquinolone, rifampicin, minocycline, bacitracin, glycopeptide, an aminoglycan antibiotic, or a mixture thereof In some examples, the at least one antibiotic comprises an aminoglycoside, gentamicin, tobramycin, or a mixture thereof. In some examples, the antibiotic(s) may be encapsulated within a microsphere. For example, the microsphere may comprise one or more proteins, polysaccharides, liposomes, biodegradable polymers, or combinations thereof.

In some examples according to the present disclosure, the liquid may be in the form of an aerosol. For example, the aerosol may be introduced into the non-thermal plasma, e.g., an afterglow region of the non-thermal plasma, before the non-thermal plasma and/or the aerosol contact the infected tissue. Additionally or alternatively, the liquid may be applied to the infected tissue as a bolus dose while contacting the infected tissue with the non-thermal plasma. The liquid may be formulated to minimize polymerization reactions. In at least one example, the liquid does not contain a material that is polymerized when the liquid contacts the plasma.

According to some aspects of the present disclosure, the antibiotic(s) is applied to the infected tissue at a dose of 1 mg/mL/min to 50 mg/mL/min. Additionally or alternatively, the antibiotic(s) may be applied for a time period ranging from about 10 seconds to about 3 minutes.

In some examples of the present disclosure, the non-thermal plasma may be operated at a frequency ranging from 200 kHz to 600 kHz, such as from 300 kHz to 575 kHz. The non-thermal plasma may be generated by a plasma device comprising an electrode, wherein applying the non-thermal plasma to the infected tissue includes maintaining a tip of the electrode at a distance of 1.0 cm to 5.0 cm from the infected tissue. In some examples, the plasma device may be coupled to a tube, wherein a proximal end of the tube contains the electrode tip of the plasma device, and a distal end of the tube is proximate the infected tissue when applying the non-thermal plasma to the infected tissue. The length of the tube may range from 2 cm to 4 cm.

In some examples, the infected tissue may include a biofilm, wherein applying the non-thermal plasma and the liquid disrupts the biofilm, such that the at least one antibiotic kills at least a portion of, or all of, the bacteria causing the infection (e.g., drug-resistant bacteria) present in the infected tissue. According to some aspects of the present disclosure, the infected tissue may include bacteria chosen from methicillin resistant *Staphylococcus aureus,* vanomycin resistant *Enterococcis,* cephalosporin resistant *Enterobacteriaciae,* or a combination thereof.

The method of treating a bacterial infection of a patient, e.g., a drug-resistant bacterial infection, according to some aspects of the present disclosure comprises generating a non-thermal plasma having a frequency between 200 kHz and 600 kHz; and introducing an aerosol into the non-thermal plasma, wherein the liquid comprises at least one antibiotic, at least one antiseptic, or a combination thereof, and a penetration enhancing agent, wherein the at least one penetration enhancing agent comprises dimethyl sulfoxide, azone, urea, an essential oil, a pyrrolidone, a fatty acid, an oxazolidinone, a terpene, a perpenoid, or a mixture thereof; and contacting infected tissue of the patient with the non-thermal plasma and the aerosol simultaneously. As mentioned above, in some examples, the liquid does not contain a material that is polymerized when the liquid contacts the plasma. Further, in some examples, the non-thermal plasma may be generated by a plasma device comprising a tube that contains an electrode tip of the plasma device, and wherein the aerosol is introduced into a first end of the tube while a second end of the tube is proximate the infected tissue.

The present disclosure also includes a method of treating a bacterial infection of a patient, e.g., a drug-resistant bacterial infection, the method comprising generating a non-thermal plasma having a frequency between 200 kHz and 600 kHz; and introducing an aerosol into the non-thermal plasma, wherein the liquid comprises at least one antibiotic and a penetration enhancing agent chosen from dimethyl sulfoxide, azone, urea, an essential oil, a pyrrolidone, a fatty acid, an oxazolidinone, a terpene, a perpenoid, or a mixture thereof; and contacting infected tissue of the patient with the non-thermal plasma and the aerosol simultaneously; wherein the infected tissue includes bacteria chosen from methicillin resistant Staphylococcus aureus, vanomycin resistant Enterococcis, cephalosporin resistant Enterobacteriaciae, or a combination thereof, and applying the non-thermal plasma and the liquid kills the bacteria.

BRIEF DESCRIPTION OF THE DRAWINGS

The accompanying drawing, which is incorporated in and constitutes a part of this specification, illustrates certain features of the present disclosure, and together with the description, serves to explain the principles of the present disclosure. Those of ordinary skill in the art will readily recognize that the features of a particular aspect or embodiment may be used in conjunction with the features of any or all of the other aspects or embodiments described in this disclosure.

FIG. 1 illustrates an exemplary system for treating a bacterial infection of a patient, in accordance with some aspects of the present disclosure.

DETAILED DESCRIPTION

The present disclosure generally includes systems, devices, and methods for treating bacterial infections in patients, including drug-resistant bacterial infections. The method may comprise applying a non-thermal plasma and at least one antibiotic and/or antiseptic to infected tissue of the patient, e.g., simultaneously. For example, the antibiotic(s) and/or antiseptic(s) may be provided as a liquid or a solid, together with a penetration enhancing agent. Further plasma treatment methods are included in the disclosure herein.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value. All ranges are understood to include endpoints, e.g., a distance between 1.0 cm and 5.0 cm includes distances of 1.0 cm, 5.0 cm, and all values between.

In some aspects, the present disclosure provides a plasma system or device designed to produce a non-thermal plasma suitable for contacting and treating wounded patient tissue while delivering one or more antibiotics to the wounded tissue. To achieve this, the plasma may be powered at a frequency ranging between 200 kHz and 600 kHz, such as between 300 kHz and 575 kHz, or between 350 kHz and 500 kHz. Such plasmas may allow for delivery of one or more antibiotics while retaining their efficacy, e.g., such that the plasma does not damage a chemical structure of the antibiotic(s) responsible for pharmaceutical and/or biological activity. Without being bound by theory, it is believed that the plasma treatment may help to treat wounded tissue and allow for greater responsiveness to antibiotic treatment, e.g., by disrupting defense mechanisms of one or more microorganisms responsible for an infection. Further, frequencies between 200 kHz and 600 kHz may provide for effective treatment without causing the patient discomfort. At frequencies lower than 200 kHz, the patient may sense the electrical discharge and feel uncomfortable, and at frequencies above 600 kHz, the stability of the plasma discharge may be decreased and the large number of discharge events (>600,000 per second) may produce excessive degradation of the antibiotic(s).

Plasmas include numerous components, such as reactive oxygen and nitrogen species, which may assist with treating drug-resistant bacterial infections. Without intending to be bound by theory, it is believed that ionized species present in the plasma may help to disrupt the cell membranes of both gram-negative and gram-positive bacteria without damaging or with minimal damage to surrounding healthy tissue. This disruption, in combination with targeted delivery of antibiotics with the plasma, may provide for effective treatment of drug-resistant bacterial infections. For example, pathogens like fungi and bacteria may be susceptible to plasma as they are bombarded with plasma components such as UV, IR, reactive oxygen species, reactive nitrogen species, electrons, ions, and/or free radicals. The plasma may also contain free radicals, UV radiation, electrons, and/or ionic species that may at least partially degrade flagella, destroy surface receptors, damage microbial DNA, disrupt bacterial biofilms, and/or kill bacteria present in such biofilms. The simultaneous delivery of antibiotics, optionally with a penetration enhancing agent, then may serve to attack the bacteria and/or other microorganisms present in infected tissue. The plasma treatments herein may help to kill various types of bacteria, including some multi-drug resistant organisms.

The one or more antibiotics delivered to infected tissue may be in liquid or solid form. Exemplary antibiotics include, but are not limited to, tobramycin, vancomycin, gentamicin, ampicillin, amoxiocillin, sulfamethoxazole/trimethoprim, carbapenem, penicillin, chloramphenicol, cephalosporin C, cephalexin, cefaclor, cefamandole and ciprofloxacin, dactinomycin, actinomycin D, daunorubicin, doxorubicin, idarubicin, penicillin, piperacillin, streptomycin, a cephalosporin, quinolone, anthracycline, mitoxantrone, a tetracycline, ticarcillin, bleomycin, plicamycin, mitomycin, polymyxin, ciprofloxacin, macrolide, fluoroquinolone, rifampicin, minocycline, bacitracin, glycopeptide, an aminoglycan antibiotic, and mixtures thereof. In some examples herein, the at least one antibiotic comprises an aminoglycoside, gentamicin, tobramycin, or a mixture thereof.

In some examples, the liquid may comprise at least one antiseptic, in addition to or as an alternative to the antibiotic(s). Exemplary antiseptics include, but are not limited to, chlorhexidine, silver compounds, povidone-iodine, iodine, hydrogen peroxide, boric acid, formaldehyde, chloroxylenol, sodium hypochlorite, benzalkonium salts, benzethonium salts, cetalkonium salts, cetalkonium chloride, quaternary ammonium salts, bisphenols such as troclosan, triclocarban, and polyhexamethylene biguanide, and combinations thereof. According to some aspects of the present disclosure, the liquid comprises at least one antibiotic, at least one antiseptic, or a combination thereof. For example, the liquid may comprise an antibiotic in combination with an antiseptic, an antiseptic without an antibiotic, or an antibiotic without an antiseptic.

In the case of antibiotics and antiseptics in liquid form, the liquid may be applied to tissue in aerosol form. For example, the antibiotic(s) and/or antiseptic(s) may be passed through a nebulizer to produce an aerosol, wherein the aerosol is then introduced into a portion of the plasma. In some examples, the liquid may consist of or consist essentially of the antibiotic(s). In some examples, the liquid may consist of or consist essentially of antibiotic(s) and antiseptic(s). In some examples, the liquid may consist of or consist essentially of antiseptic(s). In some examples, the liquid may include a carrier and other components, such as a penetration enhancing agent as discussed below. In the case of antibiotics or antiseptics in solid form, such as a dry powder, the antibiotics may be introduced into the plasma as a fine powder, for example, or the antibiotic(s) and/or antiseptic(s) may be combined with a suitable liquid carrier. For example, the dry powder antibiotic(s) and/or dry powder antiseptic(s) may be dissolved in a liquid carrier such as water, an aqueous solution, or an alcohol.

In some examples of the present disclosure, the at least one antibiotic and/or at least one antiseptic may be encapsulated within a microsphere for delivery to patient tissue. The wall of the microsphere may comprise a biocompatible material or combination of materials. Exemplary materials useful for preparing microspheres include, but are not limited to, proteins (e.g., collagen, keratin, elastin, etc.), polysaccharides (e.g., chitin, alginates, hyaluronic acid, starch, etc.), liposomes (e.g., phospholipids), biodegradable polymers (e.g., biodegradable polyesters), and combinations thereof. In some examples, the microsphere may comprise at least one protein chosen from collagen, keratin, elastin, or combinations thereof In some examples, the microsphere may comprise at least one liposome chosen from phospholipids, such as phosphatidylcholine, phosphatidylserine, or combinations thereof. In some examples, the microsphere may comprise at least one polysaccharide chosen from chitin, alginates, hyaluronic acid, starch, or combinations thereof. In some examples, the microsphere may comprise at least one biodegradable polymer chosen from poly(lactic-co-glycolic acid) (PLGA), polylactic acid (PLA), poly-L-lactic acid (PLLA), poly(2-hydroxyethyl-methacrylate), poly(ethylene glycol), polyglycine, or combinations thereof. The material forming the wall of the microsphere may be antibiotic and/or antiseptic. In at least one embodiment, the microspheres comprise an antimicrobial material, such as, e.g., a polysaccharide such as chitosan. Without being bound by theory, it is believed that the microsphere wall may protect the antibiotic(s) and/or antiseptic(s) during delivery and/or enhance the penetration capability of the antibiotic and/or antiseptic.

The average diameter of the microspheres may range from about 0.1 μm to about 500 μm, such as from about 0.1 μm to about 100 μm, from about 0.5 μm to about 100 μm, from about 1 μm to about 50 μm, from about 5 μm to about 10 μm, or from about 50 μm to about 250 μm. Microspheres may be manufactured in a variety of ways including, e.g., emulsification polymerization, phase separation or precipitation, and/or emulsion/solvent evaporation methods. Further, mechanical processes to produce microspheres include air-suspension methods, pan coating, spray drying, spray congealing, micro-orifice system, and via a rotary fluidization bed granulator.

The methods herein may include delivering the antibiotic(s) and/or antiseptic(s) together with a penetration enhancing agent. The penetration enhancing agent may comprise a substance or mixture of substances that promote migration between or across tissue layers. For example, the penetration enhancing agent may enter tissue bilayers and interrupt the adjacent lipid structures, allowing for actives formulated with the penetration enhancing agent to access infected tissues deep within a wound. The penetration enhancing agent may be selected based at least partially on compatibility with the one or more antibiotics and/or antiseptics being delivered (e.g., similar hydrophobicity or polarity characteristics) and/or the solubility of the antibiotic(s) and/or antiseptic(s) in the penetration enhancing agent. For example, the penetration enhancing agent may be in liquid form. In at least one example, the penetration enhancing agent is in liquid form, and the antibiotic(s) and/or antiseptic(s) is dissolved in the penetration enhancing agent.

Exemplary penetration enhancing agents useful for the methods herein include, but are not limited to, dimethyl sulfoxide (DMSO), azone, urea, essential oils, pyrrolidone, fatty acids, oxazolidinone, terpenes, perpenoids, and mixtures thereof. Exemplary fatty acids useful for the methods herein include, but are not limited to, caprylic acid, capric acid, lauric acid, myristic acid, palmitic acid, stearic acid, arachidic acid, oleic acid, linoleic acid, arachidonic acid, myristoleic acid, palmitoleic acid, and combinations thereof. Exemplary essential oils useful for the methods herein include, but are not limited to, garlic oil, tea tree oil, eucalyptus oil, rose oil, lavender oil, citrus oils, and combinations thereof In at least one example, the penetration enhancing agent is or comprises dimethyl sulfoxide.

According to some aspects of the present disclosure, the antibiotic(s) and/or antiseptic(s), optionally together with a penetration enhancing agent, may be formulated with a biocompatible carrier. The carrier may be in liquid form. For example, the antibiotic(s), antiseptic(s), and/or penetration enhancing agent may be at least partially soluble in the carrier. Exemplary carriers include, but are not limited to, water or an aqueous solution (including saline solution, for example), alcohols (e.g., ethanol, methanol, isopropyl alcohol, etc.), lipids, other biocompatible organic solvents, and mixtures thereof. In at least one example, the antibiotic(s) is formulated in a liquid that comprises a penetration enhancing agent and a liquid carrier, wherein one or both of the antibiotic(s) and penetration enhancing agent are at least partially or completely dissolved in the carrier. In at least one example, the liquid comprises a carrier, and optionally one or more of an antibiotic, antiseptic, or penetration enhancing agent.

In some embodiments herein, the antibiotic(s) and/or antiseptic(s) is formulated in or as a liquid that does not include a carrier. For example, the liquid may consist of or consist essentially of the penetration enhancing agent and one or more antibiotics. Further, for example, the liquid may consist of or consist essentially of the penetration enhancing agent, one or more antibiotics, and one or more antiseptics. In some examples, the liquid may consist of or consist essentially of the penetration enhancing agent and one or more antiseptics.

Each of the antibiotic(s), antiseptic(s), penetration enhancing agent, and carrier may be selected to include only molecules and/or materials that do not readily undergo chemical bond forming reactions in a plasma environment. For example, the antibiotic(s) and/or antiseptic(s) may be formulated to minimize polymerization reactions, e.g., such that the activity of the antibiotic(s) and/or antiseptic(s) is retained during exposure to the plasma. In the case of applying the antibiotic(s) and/or antiseptic(s) as a liquid (e.g., aerosol), for example, the liquid may be formulated to minimize unsaturated compounds or components. In at least one example, the liquid does not contain a material that is polymerized when the liquid contacts the plasma. In some examples herein, the penetration enhancing agent does not contain vinyl groups, acrylate groups, or other forms of unsaturated functional groups. In at least one example, the penetration enhancing agent contains minimal levels of unsaturated bonds such as vinyl or acrylate functional groups, such as only 1 or 2 unsaturated functional groups per molecule. Additionally or alternatively, the antibiotic(s), antiseptic(s), and/or carrier may be selected to exclude or minimize the presence of unsaturated functional groups.

The methods herein may be performed by using a plasma device (or plasma system) to generate the non-thermal plasma. For example, the plasma device may comprise one or more electrodes and an ignition system operatively connected to the electrodes for providing a non-thermal equilibrium plasma. The plasma device may further comprise a gas supply inlet configured to receive a suitable type of gas to sustain the plasma, e.g., an inert or semi-insert gas such as helium, argon, nitrogen, air, etc. For example, the plasma may be generated at atmospheric pressure. The device may comprise an argon plasma coagulator or a helium plasma coagulator.

The plasma device may include a chamber exposed to ambient pressure, wherein the non-thermal equilibrium plasma may be generated within the chamber. The chamber may have an open end to be positioned proximate to wounded tissue during use, such that the plasma may be applied to tissue. The length (and volume) of the chamber may be fixed, or the length of the chamber may be adjustable. For example, the walls of the chamber may allow for adjusting the distance between the tip of the electrode used to generate the plasma and the open end of the chamber. Such adjustability may allow a user to adjust the distance between the electrode tip and the patient tissue to be treated (increasing or decreasing the distance), according to the needs of the patient.

FIG. 1 illustrates an exemplary plasma system 100 that may be used to perform the methods herein, e.g., to treat a bacterial infection of a patient, such as a drug-resistant bacterial infection. While the system 100 is described herein as having a given configuration and components, it will be apparent to those of ordinary skill in the art that variations of system 100 are also encompassed herein. For example, any components of system 100 may be arranged in a different configuration or order, or may be omitted completely. Further, additional components may be added to the system 100.

System 100 as shown includes a plasma device 102 for generating a non-thermal plasma 104. The device 102 may be coupled to a tube 108 that defines a chamber in which the plasma 104 is generated, wherein the proximal end of the tube 108 contains an electrode tip 106 of the device 102. The electrode may be a monopolar electrode. The configuration of the chamber may avoid quenching the plasma 104 by atmospheric air and may help to stabilize the plasma 104.

In some examples, as shown in FIG. 1, the system 100 may include a structure, e.g., a barrier 110 at the proximal end of the tube 108. The barrier 110 may comprise a non-conductive material, e.g., a polymer or ceramic material. Exemplary materials include, but are not limited to, polyethylene, polypropylene, polytetrafluoroethylene (e.g., Teflon), alumina, silica, and polycarbonate. The plasma 104 generated from the electrode tip 106 is contained within the volume of the tube 108 and exits the distal, open end of the chamber. The barrier 110 may define an aperture through which the distal end of the device 102 extends. In some examples, the barrier 110 may be omitted. The distal end of the tube 108 may be positioned proximate to infected tissue 112 of a patient.

The system 100 as shown also includes a nebulizer 114 that may be used to generate an aerosol 116 for application to the tissue 112 together with the plasma 104. The nebulizer 114 may include an inlet that receives a supply of a liquid, which then is aerosolized as it exits an outlet of the nebulizer 114. The outlet of the nebulizer may be in communication with the chamber of the system 100, e.g., the distal end of the nebulizer 114 being adjacent to the barrier 110, and the barrier 110 defining an aperture through which the distal end of the nebulizer 114 extends. Thus, the aerosol 116 exiting the nebulizer 114 are introduced into the plasma 104 within the chamber prior to the aerosol 116 and the plasma 104 contacting the tissue 112. While FIG. 1 illustrates a configuration in which the nebulizer 114 is generally parallel to the walls of the tube 108 and parallel to the device 102, other configurations may be used. For example, the nebulizer 114 may be positioned perpendicular (or otherwise transverse) to the device 102, such that the aerosol 116 enters the plasma 104 from a transverse direction. In such cases, the nebulizer may be coupled to any suitable location along the tube 108, e.g., proximate the proximal end of the tube 108, toward a central region of the tube 108, or proximate the distal end of the tube 108.

In use, the electrode tip 106 may be within a few centimeters or millimeters of the patient tissue. As mentioned above, the length of the chamber defined by the tube 108 may be fixed or adjustable. In some embodiments, the length of the tube 108 may range from about 1 cm to about 5 cm, such as from about 1.5 cm to about 4.5 cm, or from about 2 cm to about 4 cm. The length of the tube may be manufactured or cut to a desired length. By altering the length of the tube 108, the distance of the electrode tip 106 from the patient tissue may be controlled, which in turn allows for controlling exposure of the tissue to the plasma 104. For example, a user may increase or decrease the length of the tube 108 to decrease exposure and/or change the type of species that reach the tissue. Increasing the length of the tube is expected to increase the residence time of the active species within the plasma and therefore increase plasma activation of the antibiotic(s), antiseptic(s), and/or carrier, depending on the region of the plasma in which the antibiotic(s), antiseptic(s), and/or carrier are introduced. Increasing the length of the tube also increases the distance of the electrode from the target tissue to be treated, allowing short-lived species such as free radicals, singlet oxygen, and/or ionic species to decay before reaching the patient tissue. Additionally, increasing the length of the tube is believed to decrease the risk of harming the patient due to arcing, e.g., by lessening the potential for the powered electrode to form an arc that may hit the patient and damage tissue. In this way, the user may avoid exposing the tissue to plasma in a form that would cut, burn, or ablate the tissue. Without being bound by theory, it is believed that as the inert or semi-inert gas flows from the electrode tip 106 during generation of the plasma, the gas may purge the volume of the chamber and displace air, thus stabilizing the plasma 104. Similarly, shortening the length of the tube can bring the electrode closer to the tissue and create a more intense (e.g., energetic) plasma, thereby allowing the plasma to actively cut, ablate, and/or debride the infected tissue.

According to some examples herein, the distance between the electrode tip 106 and the patient tissue may be greater than 5 mm, to avoid damage to the tissue. For example, in some embodiments of the present disclosure, the electrode tip 106 may be at least 1.0 cm, but less than 5 cm from the tissue when applying the non-thermal plasma and delivering the antibiotic(s). For example, the electrode tip 106 may be located at a distance of about 1.5 cm to about 2.0 cm from the tissue. The patient may also be connected to a grounded electrode with a contact area between the ground electrode and the patient of at least 20 cm$^2$.

When the antibiotic(s) and/or antiseptic(s) are formulated in liquid form (optionally with a penetration enhancing agent and/or carrier), the liquid may be nebulized using any appropriate atomizer or nebulizer, including, e.g., ultrasonic, piezo, pneumatic, mechanical, electrical, vibrating mesh, or jet nebulizers. Similarly, a carrier liquid with or without antibiotic(s) and/or antiseptic(s) may be nebulized for wound irrigation, as further described below. In some embodiments of the present disclosure, the flow of gas used to generate the plasma may range from about 4 liters/min (L/min) to about 10 L/min, such as from about 4 L/min to about 6 L/min. Gas flows below 4 L/min may give rise to a prolonged residence time of the antibiotic(s) and/or antiseptic(s) in the chamber, which may increase a risk of fragmentation and/or polymerization of one or more components of the liquid (the active antibiotic(s), antiseptic(s), penetration enhancing agent, and/or carrier). Further, gas flows above 10 L/min may provide insufficient time for the antibiotic(s) and/or antiseptic(s) to migrate through infected tissue, e.g., washing the antibiotics and/or antiseptic(s) away from the tissue surface too quickly.

In some examples, infected tissue may be treated with a plasma-activated carrier liquid. For example, the liquid may comprise a saline solution, wherein introducing the liquid into the plasma allows the plasma to interact with the solution to produce a plasma-activated aqueous solution that is then sprayed onto the wound (e.g., infected tissue). Such a plasma-activated solution may comprise a range of radicals and/or other species that may also reduce bacterial loading of infected tissue. The aqueous solution also may comprise antibiotics, antiseptics, and/or a penetration enhancing agent, which may enhance antimicrobial activity of the plasma-activated water.

In some examples, the non-thermal plasma may be combined with a nebulized liquid and used to debride the wound, e.g., removing necrotic infected tissue while simultaneously spraying a flow of aerosol droplets (comprising a carrier liquid, antibiotic(s), antiseptic(s), and/or penetration enhancing agent) to irrigate and cleanse the wound. In these examples, the flow of liquid droplets may cool the wound while the plasma is applied, thereby minimizing thermal damage to the tissue from the plasma. The combination of non-thermal plasma and antimicrobial and/or antiseptic wound irrigation may act synergistically to reduce the levels of bacterial burden at the wound site. In some examples, different flow rates may be used for wound irrigation (e.g., a carrier introduced into plasma) prior to applying the antibiotic(s) and/or antiseptic(s) (e.g., a liquid comprising one or more antibiotic(s) and/or antiseptic(s), optionally with a penetration enhancing agent and/or a carrier).

In at least one aspect, the plasma is a pulsed plasma. The plasma may be pulsed at various duty cycles such that the power delivered is less than 100 W, e.g., less than 50 W. The pulsing may be such that the applied power is off for at least 50% of the time, e.g., with the pulses switched on and off many times per second. For example, the plasma may be pulsed on and off to deliver an on-time ranging from about 1 nanosecond (ns) to about 500 milliseconds (ms). For example, the plasma may be pulsed with an on-time ranging from 1 ms to 500 ms, such as from 10 ms to 300 ms, from 50 ms to 100 ms, e.g., an on-time of about 1 ms, about 10 ms, about 50 ms, about 75 ms, about 100 ms, about 200 ms, about 250 ms, about 300 ms, about 400 ms, or about 500 ms. In some aspects of the present disclosure, the plasma may be pulsed with an on-time ranging from 1 ns to 500 ns, such as from 10 ns to 300 ns, 50 ns to 100 ns, e.g., an on-time of about 1 ns, about 10 ns, about 50 ns, about 75 ns, about 100 ns, about 200 ns, about 250 ns, about 300 ns, about 400 ns, or about 500 ns.

In at least one embodiment, the liquid comprising the antibiotic(s) and/or antiseptic(s) (and optionally a penetration enhancing agent and/or carrier) may be introduced into the plasma at various locations. In some examples, the liquid, e.g., in aerosol form, may be introduced into the plasma downstream of the electrode tip. For example, the liquid may be in indirect contact, rather than direct contact, with higher energy regions of the plasma. By introducing the liquid downstream or in the afterglow region containing long-lived plasma species, potentially degrading effects of the plasma due to shorter-lived species may be minimized.

In some embodiments of the present disclosure, the liquid that comprises the antibiotic(s) (optionally with a penetration enhancing agent and/or carrier) may be passed through an atomizer/nebulizer at a flow rate of at least 50 microlitres/min (μL/min), at least 100 μL/min, or at least 120 μL/min. For example, the flow rate may range from about 60 μL/min to about 500 μL/min, from about 80 μL/min to about 300 μL/min, or from about 100 μL/min to about 250 μL/min. In some examples, the flow rate used for the nebulizer does not exceed 1 ml/min. For example, the flow rate may be less than 500 μL/min or less than 250 μL/min.

According to some aspects of the present disclosure, higher flow rates are used, such as for wound irrigation. In such cases, the liquid may be dispensed from a needle or other lavage device, for example. The flow rate of the liquid may be at least 1 mL/min, e.g., within a range of about 1 mL/min to about 5000 mL/min. For example, the flow rate may range from about 100 mL/min to about 5,000 mL/min, or from about 500 mL/min to about 1000 mL/min. The methods herein may include irrigating the wound before, during, and/or after applying antibiotic(s) and/or antiseptic(s). As discussed above, the liquid used for wound irrigation may comprise a liquid carrier, such as saline solution or other biocompatible liquid, wherein the liquid may be introduced into the non-thermal plasma to activate the carrier liquid.

According to some examples herein, the liquid is applied to the infected tissue as a bolus dose from a suitable receptacle while contacting the infected tissue with the non-thermal plasma. For example, the antibiotic(s) and/or antiseptic(s) (optionally in combination with a penetration enhancing agent and/or carrier) may be applied to patient tissue as a single dose of at least 1 mg before, during, or after treating the tissue with plasma. In some examples, the antibiotic(s) and/or antiseptic(s) are not delivered as a bolus dose. For example the antibiotic(s) may be delivered constantly or consistently for as long as the non-thermal plasma is applied to the tissue.

Without being bound by theory, it is believed that the antibiotic levels are delivered such that the overall systemic levels of antibiotic remains low, but the local concentration of antibiotic in the target wound area is sufficient to inhibit bacterial proliferation.

In some examples of the present disclosure, each antibiotic or antiseptic may be applied to the infected tissue at a dose of about 1 mg/mL/min to about 50 mg/mL/min, such as from about 2 mg/mL/min to about 10 mg/mL/min. When multiple antibiotics and/or antiseptics are applied, the dose of each antibiotic or antiseptic may be the same, or the doses may vary, according to the needs of the patient. Further, for example, the antibiotic(s) and/or antiseptic(s) may be applied for a time period ranging from about 10 seconds to about 3 minutes on a target area or region of tissue. In at least one embodiment, the dose of one or more antibiotics or antiseptics does not exceed 20 mg/mL/min. A prolonged treatment may enhance the penetration effect and maximize the plasma contribution to killing bacteria present in the tissue and/or otherwise sterilizing the wound. In at least one embodiment, the target area may be treated for about 15 seconds per dose to about 60 seconds per dose. In some examples herein, multiple doses may be applied at various times throughout a single day (e.g., every 12 hours, every 6 hours, every 2 hours, two doses within 30 minutes, etc.), or on separate days (e.g., every other day, once a week, twice a week, three times a week, etc.). The appropriate dose of antibiotic may be selected based on the nature of the antibiotic and the extent of the infection.

In some embodiments of the present disclosure, the methods herein may be used to treat infected tissue due to bacteria of genera including, but not limited to, *Enterococci, Escherichia, Pseudomonas, Klebsiella, Enterobacter, Proteus, Acinetobacter*, or a combination thereof. For example, the infected tissue may include one or more strains or species of bacteria including, but not limited to, *Staphylococcus aureus, Staphylococcus epidermidis, Corynebacterium, Brevibacterium, Propionibacterium acnes, Pityrosporum, Streptococcus pyogenes, Streptococcus agalactiae, Escherichia coli, Enterobacteriaciae, Stenotrophomonas, Pseudomonas aeruginosa*, or a combination thereof. Further, for example, the methods herein may be used to treat drug-resistant (antibiotic resistant) strains of these bacteria. Such bacteria may include, but are not limited to, methicillin resistant *Staphylococcus aureus*, vanomycin resistant *Enterococcis*, cephalosporin resistant *Enterobacteriaceae*, or a combination thereof.

In some examples, the infected tissue may include a biofilm. As discussed above, applying the non-thermal plasma and the antibiotic(s) and/or antiseptic(s) (optionally in combination with a penetration enhancing agent and/or carrier) may at least partially disrupt the biofilm, such that the antibiotic(s) can penetrate the biofilm, penetrate more deeply into the infected tissue, and kill bacteria present in the infected tissue.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents that all fall in the scope of the aspects described herein. Accordingly, the present disclosure is not to be considered as limited by the foregoing description.

What is claimed is:

1. A method of treating a bacterial infection of a patient, the method comprising:
    applying a non-thermal plasma and a liquid simultaneously to infected tissue of the patient, the liquid comprising at least one antibiotic and a penetration enhancing agent chosen from dimethyl sulfoxide, azone, urea, an essential oil, a pyrrolidone, an oxazolidinone, a terpene, a perpenoid, or a mixture thereof;
    wherein the liquid penetrates the infected tissue of the patient, and
    wherein the non-thermal plasma has a frequency between 200 kHz and 600 kHz.

2. The method of claim 1, wherein the liquid comprises a carrier chosen from water, an alcohol, a lipid, an organic solvent, or a mixture thereof, and wherein the at least one antibiotic, the penetration enhancing agent, or both the at least one antibiotic and the penetration enhancing agent are dissolved in the carrier.

3. The method of claim 1, wherein the penetration enhancing agent comprises dimethyl sulfoxide.

4. The method of claim 1, wherein the infected tissue includes drug-resistant bacteria.

5. The method of claim 1, wherein the at least one antibiotic is selected from the group consisting of tobramycin, vancomycin, gentamicin, ampicillin, amoxiocillin, sulfamethoxazole/trimethoprim, carbapenem, penicillin, chloramphenicol, cephalosporin C, cephalexin, cefaclor, cefamandole and ciprofloxacin, dactinomycin, actinomycin D, daunorubicin, doxorubicin, idarubicin, penicillin, piperacillin, streptomycin, a cephalosporin, quinolone, anthracycline, mitoxantrone, a tetracycline, ticarcillin, bleomycin, plicamycin, mitomycin, polymyxin, ciprofloxacin, macrolide, fluoroquinolone, rifampicin, minocycline, bacitracin, glycopeptide, an aminoglycan antibiotic, and mixtures thereof.

6. The method of claim 1, wherein the at least one antibiotic is encapsulated within a microsphere.

7. The method claim 6, wherein the microsphere comprises a material selected from the group consisting of a protein, a polysaccharide, a liposome, a biodegradable polymer, and combinations thereof.

8. The method of claim 1, wherein the liquid is in the form of an aerosol, and the aerosol is introduced into an afterglow region of the non-thermal plasma before the non-thermal plasma and the aerosol contact the infected tissue.

9. The method of claim 8, wherein the liquid does not contain a material that is polymerized when the aerosol is introduced into the plasma.

10. The method of claim 1, wherein the liquid is applied to the infected tissue as a bolus dose of at least 1 mg while contacting the infected tissue with the non-thermal plasma.

11. The method of claim 1, wherein the at least one antibiotic is applied to the infected tissue at a dose ranging from 1 mg/mL/min to 50 mg/mL/min for a time period ranging from 10 seconds to 3 minutes.

12. The method of claim 1, wherein the non-thermal plasma is operated at a frequency ranging from 300 kHz to 575 kHz.

13. The method of claim 1, wherein the non-thermal plasma is generated by a plasma device comprising an electrode, and applying the non-thermal plasma to the infected tissue includes maintaining a tip of the electrode at a distance ranging from 1.0 cm to 5.0 cm from the infected tissue.

14. The method of claim 1, wherein the non-thermal plasma is generated by a plasma device coupled to a tube, a proximal end of the tube containing an electrode tip of the plasma device, and a distal end of the tube being proximate the infected tissue when applying the non-thermal plasma to the infected tissue, the electrode tip being inside the tube and proximal to the distal end of the tube.

15. The method of claim 14, wherein the length of the tube is in a range from 2 cm to 4 cm, and the electrode tip is maintained at a distance ranging from 1.0 cm to 5.0 cm from the infected tissue.

16. The method of claim 1, wherein the infected tissue includes a biofilm, and applying the non-thermal plasma and the liquid disrupts the biofilm, such that the at least one antibiotic kills bacteria present in the infected tissue.

17. The method of claim 1, wherein the infected tissue includes bacteria chosen from methicillin resistant *Staphylococcus aureus*, vanomycin resistant *Enterococcis*, cephalosporin resistant *Enterobacteriaciae*, or a combination thereof.

18. A method of treating a bacterial infection of a patient, the method comprising:
   generating a non-thermal plasma with a plasma device, the non-thermal plasma having a frequency between 200 kHz and 600 kHz; and
   introducing a liquid aerosol into the non-thermal plasma, wherein the liquid aerosol comprises:
      at least one antibiotic, at least one antiseptic, or a combination thereof; and
      at least one penetration enhancing agent, wherein the at least one penetration enhancing agent is chosen from dimethyl sulfoxide, azone, urea, an essential oil, a pyrrolidone, a fatty acid, an oxazolidinone, a terpene, a perpenoid, or a mixture thereof, and
   contacting infected tissue of the patient with the non-thermal plasma and the liquid aerosol simultaneously while maintaining an electrode tip of the plasma device at a distance ranging from 1.0 cm to 5.0 cm from the infected tissue, wherein the infected tissue includes drug-resistant bacteria and the liquid aerosol deposits on the infected tissue in liquid form and penetrates the infected tissue.

19. The method of claim 18, wherein the no plasma device comprises a tube that contains the electrode tip of the plasma device, and wherein the liquid aerosol is introduced into a first end of the tube while a second end of the tube is proximate the infected tissue.

20. A method of treating a bacterial infection of a patient, the method comprising:
   generating a non-thermal plasma having a frequency between 200 kHz and 600 kHz using a plasma device coupled to a tube, a proximal end of the tube containing an electrode tip of the plasma device, wherein the length of the tube is adjustable in a range from 2 cm to 4 cm;
   introducing a liquid aerosol into the non-thermal plasma, wherein the liquid aerosol comprises at least one antibiotic and a penetration enhancing agent; and
   contacting infected tissue of the patient with the non-thermal plasma and the liquid aerosol simultaneously, a distal end of the tube of the plasma device being proximate the infected tissue when applying the non-thermal plasma to the infected tissue;
   wherein the infected tissue includes drug-resistant bacteria chosen from *Acinetobacter baumannii, Pseudomonas aeruginosa, Enterobacteriaceae, Staphylococcus aureus, Clostridium difficile*, or a combination thereof, the liquid aerosol deposits on the infected tissue as a liquid that penetrates the infected tissue, and wherein applying the non-thermal plasma and the liquid aerosol kills the drug-resistant bacteria.

* * * * *